United States Patent [19]

Ueda et al.

[11] Patent Number: 5,044,091

[45] Date of Patent: Sep. 3, 1991

[54] METHOD OF PREPARING A FREEZE-DRIED FORMULATION CONTAINING A DRUG

[75] Inventors: Seigo Ueda; Kunio Hashi; Takashi Shiokari; Akira Kusai, all of Shinagawa, Japan

[73] Assignee: Sankyo Company, Limited, Tokyo, Japan

[21] Appl. No.: 509,967

[22] Filed: Apr. 16, 1990

[30] Foreign Application Priority Data

Apr. 18, 1989 [JP] Japan ................... 1-98561

[51] Int. Cl.$^5$ ............................... F26B 5/06
[52] U.S. Cl. ........................... 34/5; 34/15; 34/92
[58] Field of Search .................... 34/4, 5, 15, 92

[56] References Cited

U.S. PATENT DOCUMENTS

| 4,430,807 | 2/1984 | Davis et al. | 34/15 |
| 4,433,558 | 2/1984 | Cheng et al. | 34/5 |
| 4,470,202 | 9/1984 | Buxton et al. | 34/5 |

FOREIGN PATENT DOCUMENTS

| 0211257 | 2/1987 | European Pat. Off. |
| 61-68412 | 4/1986 | Japan . |
| 62-29513 | 2/1987 | Japan . |

OTHER PUBLICATIONS

Williams et al., "The Lyophilization of Pharmaceuticals: A Literature Review", J. Parenteral Science and Technology, 38, pp. 48–59 (1976).

Koyama et al., "Effect of Solvent Addition and Thermal Treatment on Freeze Drying of Cefazolin Sodium", J. Parenteral Science and Technology, 42, pp. 47–52 (1988).

Journal of the Research Society of Freezing and Drying, 22, pp. 48–55 (1976).

Farumashi, 5, pp. 99–102, vol. 5, No. 2, Feb. 1969.

Primary Examiner—Henry C. Yuen
Attorney, Agent, or Firm—Frishauf Holtz Goodman & Woodward

[57] ABSTRACT

In a freeze-drying method for producing a dried pharmaceutical compound or preparation, a first liquid is frozen, a second liquid is added to the frozen first liquid and is frozen thereon, and the frozen first and second liquids are freeze-dried together, in which at least one of said first and second liquids contains said pharmaceutical compound of preparation dissolved or suspended therein. The other liquid or liquids may be pure solvent (generally water) or may contain one or more other substances.

34 Claims, No Drawings

METHOD OF PREPARING A FREEZE-DRIED FORMULATION CONTAINING A DRUG

BACKGROUND OF THE INVENTION

The present invention relates to a method of preparing a freeze-dried (or "lyophilized") formulation containing a drug or a mixture of drugs, which enables the freeze-drying technique to be used even in many cases where freeze-drying has hitherto not been practical, for example in the case of drugs which can be freeze-dried only with difficulty in a single solution, or whose stability is reduced when two or more components are mixed in a single solution.

Preparation of dried formulations by freeze-drying has been widely used for a variety of pharmaceutical preparations, and much research has been carried out in an attempt to determine how various problems associated with the technique may be overcome. A general review of the freeze-drying techniques used for pharmaceuticals may be found in "The Lyophilization of Pharmaceuticals: A Literature Review" by N.A. Williams and G.P. Polli, J. Parenteral Science and Technology, 38, 48-55 (1976), the disclosure of which is incorporated herein by reference. Other specific techniques or processes for freeze-drying specific drugs are disclosed in Japanese Patent Application Kokai No. 68412/1986, J. Parenteral Science and Technology, 42, 47-52 (1988) and European Patent Application No. 211 257, the disclosures of which are incorporated herein by reference.

In essence, freeze-drying consists of at least two steps:
1. Freezing a solution or suspension (almost invariably aqueous) of the material to be freeze-dried; and
2. Raising the temperature of the frozen material so that the frozen solvent (almost invariably ice) sublimes without melting.

Freeze-dried formulations are often mixtures of two or more active ingredients, and various other components, such as vehicles, stabilizers, isotonic agents, etc., other than the active ingredients, may be added in many cases. However, the eutectic temperature of the system during freezing changes with the nature of the additives, and, in particular, the addition of an inorganic substance will often markedly lower the eutectic point [Arimoto et al, "Journal of The Research Society of Freezing and Drying", 22, 48-55 (1976)]. Also, if the aqueous solution of a principal drug has a low eutectic point, further lowering of the eutectic point may sometimes occur as a result of the inclusion of additives [Arimoto et al, "Journal of The Research Society of Freezing and Drying", 22, 48-55 (1976)].

In general, a freeze-dried composition can be prepared by freeze-drying the frozen composition at a product temperature not higher than the eutectic point, and this will give a freeze-dried product having a good appearance (N. A. Williams et al, op. cit.), but the appearance of the freeze-dried product becomes less desirable, and it may even appear syrupy, if the freeze-drying is carried out at a temperature higher than the eutectic point [Koji Ito et al. Farumashia, 5, 99 (1969)], which markedly impairs its commercial value. In practice, however, in order to increase the freeze-drying speed, it is desirable that the drying shelf temperature (and hence the product temperature) should be set at as high a temperature as possible. However, when the solution to be dried contains several different kinds of solute components, because this lowers the eutectic point, it is not easy to increase the drying temperature by very much. Accordingly, freeze-drying of a drug having a low eutectic point has to be carried out at a low temperature, but this means that the primary drying process must be effected for a long time, which adversely affects the economics of the freeze-drying process.

Various contrivances have been proposed in order to increase the speed of freeze-drying. For example, the drying speed may be considerably increased by increasing the size of the frozen ice crystals by performing a certain specific thermal treatment during freezing [see, for example, Japanese Patent Application Kokai No. 68412/1986, and J. Parenteral Science and Technology, 42, 47-52 (1988)]. Another way of increasing the speed of freeze-drying is to increase the surface area available for evaporation of moisture. In the case of a drug, where the freeze-drying normally takes place in the vial in which the drug is to be sold (for improved sterility), this may be achieved by freezing over the wall surface of the vial, with the vial containing the liquid to be freeze-dried being kept horizontal to increase the surface area and by using any of several techniques, for example: by using an automatic shell-freezer model (Virtis); by freezing to the wall surface of the vial, whilst subjecting it to high speed rotation, e.g. using a centrifugal freeze dryer model EF6 (Edwards); or by freezing and drying to form granules by adding the aqueous solution to be freeze-dried dropwise to a very cold refrigerant fluid (e.g., a fluorocarbon) or to liquid nitrogen, e.g., as described in Japanese Patent Application Kokai No. 29513/1987.

However, although low temperature drying may be achieved by the methods described above, the appearance of the dried product is frequently less than desirable or a partially syrupy dried product may be obtained. The product referred to herein as "syrupy" is a product in which a small amount of water remains, so that some part of it may resemble a syrup or a gum.

Another problem often encountered in freeze-drying is that some drugs are unstable at pH values in the region where they may be administered to the living body, but are stable in acidic or alkaline solutions. These drugs have to be formed into pharmaceutical preparations, whilst in the acidic or alkaline state, and must then be restored to around neutrality at the point of administration. For this reason, a freeze-dried preparation of this kind which, when dissolved, would have a pH outside the range that could safely or comfortably be administered to the human body is often provided to the ultimate user in association with an aqueous solution containing the necessary amount of an alkali or an acid, respectively, in order to achieve a suitable pH value. Examples of such preparations include: a preparation in which a sodium monohydrogenphosphate solution is provided in association with ademethionine (see Example 2, hereafter); and a preparation in which a sodium monohydrogenphosphate solution is provided in association with a carboquone freeze-dried product. This provision of a solution of a compensatory acid or alkali also has disadvantages of production cost, and expansion of the volume of the total preparation leads to an increase in the necessary storage space, which is undesirable to both distributors and users of pharmaceuticals.

The only method known in the prior art to overcome this drawback was to avoid the freeze-drying method and to divide the drug and the neutralizing agent in the form of powders, as such into small portions which are then placed in the vials or other vessels. However, such a powdery divided preparation has many disadvantages as compared with a freeze-dried preparation. For example: (1) it is difficult to measure small amounts accurately and reproducibly; (2) contamination may occur; (3) stability may be reduced due to the increase in the area of contact between the different components, because they were mixed in the powdery state; and (4) it is very difficult to divide strongly hygroscopic powders.

It can be seen from the above discussion that it is desirable to shorten the drying time of freeze-dried preparations, in order to reduce the production cost, in order to give a high quality preparation, and in order to improve the appearance of the freeze-dried product.

Also, for drugs which become unstable through interaction with one or more other components of the formulation, the technique used at present depends on divided preparations, but, in view of the problems of powdery divided preparations, freeze-dried preparations are preferred.

In particular in the case of the mass production of pharmaceuticals, for which sterile operation is required, these problems must be overcome.

BRIEF SUMMARY OF INVENTION

It is, therefore, an object of the invention to provide a new and improved freeze-drying process.

It is a further object of the invention to provide a freeze-drying process which, when carried out in accordance with the preferred embodiments described herein, enables the above disadvantages of the prior art processes to be overcome.

In accordance with the present invention, there is provided a method of preparing a freeze-dried preparation in which a first liquid is frozen, a second liquid is added to the frozen first liquid and is frozen thereon, and the frozen first and second liquids are freeze-dried together, in which at least one of said first and second liquids contains a pharmaceutical compound or preparation dissolved or suspended therein.

DETAILED DESCRIPTION OF INVENTION

There is no restriction on the nature of the pharmaceutical compound or preparation employed in the process of the present invention, and the invention is, in principle, applicable to any therapeutic or otherwise physiologically active compound, including drugs of many sorts (e.g., antibiotics, analgesics, anti-inflammatory agents, anti-cancer drugs and many others), vitamins and the like. These are referred to simply by way of example, and the method can be applied to many other pharmaceutical compounds and preparations.

Thus, we have now found that the freeze-drying speeds of individual freeze-drying solution systems can be raised noticeably by freezing the solute components in the form of several separate solutions. More specifically, we have found that, if a plurality of frozen solutions or other liquids in several layers is freeze-dried, the freeze-drying temperature can be set higher than if all of the components were present in a single solution, which, of course, increases the drying speed. A further advantage appears in the case of mixtures of several components: these can be formed into a freeze-dried preparation, by putting one or more of the components into each frozen layer, and there is no need to prepare separately divided preparations. Moreover, the process of the present invention helps to provide a more stable pharmaceutical preparation than do conventional processes: when the stability of a drug is 90% or less at 40° C. over a period of 6 months, it cannot be used in practice in most cases. The process of the present invention is capable, in the cases tested, of providing improved stability for combinations of drugs so that they can achieve the stability necessary for practical use.

In carrying out the process of the present invention, there are employed at least two frozen layers of different liquids. However, more layers than this may be used, depending upon the particular requirements of the product which it is desired to prepare. For example, if the product contains two components, there may be two layers (in which each layer contains one of the components) or three layers (in which each of the components is in a separate layer and the third layer may be, for example, plain water, to assist the speed of the freeze-drying process). If the product contains three components, there may be two layers (all three components in one layer and plain water in the other), three layers (each component in a separate layer, or two components in one layer, one in another and plain water in the third) or four layers (each component in a separate layer, and plain water in the fourth). Other combinations are obviously possible and are within the scope of the present invention. There is no theoretical maximum number of layers, and the only considerations limiting the number of layers are practical: the minimum depth of each layer and the maximum depth of the combined layers for efficient freeze-drying, as described in more detail hereafter. In general, however, we would not recommend more than three layers, as more than this could give rise to practical difficulties.

The freeze-drying process of the present invention is normally carried out in a container, which, for convenience is normally and preferably the same container as the material is to be supplied in, normally a vial or similar medical container. However, the nature of the container is of no relevance to the present invention and the container may be chosen having due regard to the usual considerations employed in conventional freeze-drying processes.

In a preferred embodiment of the present invention, freezing is carried out by apportioning an appropriate amount of a first liquid into the container to be used for freeze-drying, such as vial or the like and freezing it, which may be by any known method, for example in a freezer or a freeze-drier or by dipping it in a refrigerant such as acetone/dry ice or liquid nitrogen. The temperature to which the first liquid is frozen should be such that the frozen liquid of the first layer does not melt and mix with the second liquid when the second liquid is added. Generally, a temperature in the range of from $-10°$ C. to $-50°$ C. is preferred, but lower temperature may be used, provided that no harm results to the drug. The temperature is more preferably from $-30°$ C. to $-50°$ C. and is most preferably about $-40°$ C.

After adding the second layer, this is then frozen, which may be achieved by any known method, for example by any of the methods suggested above for freezing the first layer or simply by conventional means used in ordinary freeze-drying processes.

If three or more frozen layers are to be formed, addition of the subsequent liquid or liquids and their subsequent freezing may be carried out in a similar way, always ensuring that there is no or is no appreciable melting of the previously frozen liquid or liquids.

Where there are two layers, there is no need to use any particular freezing technique or temperature for the second layer, and it is possible to use merely those techniques and temperatures which are conventional for freeze-drying. The same applies to the last of the layers where there are three or more layers.

There is no particular restriction on the amount of liquid added and frozen for each layer, and this will clearly depend on the amount of the drug or other material which it is desired to include, as well as upon its concentration in the respective solution. In practice, because of the required time for drying (which will depend also on the bottom area of the container, such as the vial, to be used), the total thickness of the frozen layers is preferably 40 mm or less. Hence, the maximum thickness of each layer should preferably be so chosen that the total thickness does not exceed 40 mm. The minimum thickness, on the other hand, depends on the amount of material to be used, its concentration in the solution and the practical difficulty of adding accurately small amounts of liquid. In general, we prefer that the minimum thickness of each layer should be 1 mm, and it is preferably not less than 2 mm.

When freezing more than one kind of liquid to form a laminated frozen structure, there is no general guide to the best order in which the liquids must be added. If it is observed in practice that the order of addition has an effect in any particular case on such factors as the quality of the product or the drying speed, then the order of addition may be changed as desired, but this can easily be done as part of the routine work of the common technician.

Once all of the liquids necessary have been added, the container containing the frozen liquids is placed in a freeze-drier. The conditions for freeze-drying may be the same as in a conventional freeze-drying process and there are no particular restrictions peculiar to the method of the present invention.

It is not necessary that all of the liquids frozen in accordance with the present invention should be solutions, and one or more (but not all) may be a pure solvent (generally and preferably water). When pure water containing no solute component at all is frozen to form one layer, and then a desired solution is added to it and frozen and dried, we have most unexpectedly found that the drying speed can be most remarkably increased.

The freeze-dried preparation after the primary drying and secondary drying steps clearly shows the appearance of two or more fractionated layers.

Generally speaking, the appearance of the freeze-dried products obtained in accordance with the present invention was found to be good.

The invention is further illustrated with reference to the following non-limiting Examples.

EXAMPLE 1

Preparation of a freeze-dried drug which can usually be dried only with difficulty 5 ml of a 10% w/v aqueous solution of N-benzoyl-$\beta$-alanine (an adjuvant) (exhibiting a eutectic point of $-36°$ C.) was charged into a 20 ml vial, and frozen in a freezing chamber at $-40°$ C. for 60 minutes to form a lower layer. Separately, 5 ml of a 10% w/v aqueous solution of (5R, 6S, 8R)-2-[(3S)-1-acetimidoylpyrrolidin-3-yl-thio]-6-(1-hydroxyethyl)-2-carbapenem-3-carboxylic acid (the main drug, an antibiotic) was cooled to 5° C., and this cooled solution was then added onto the frozen layer of N-benzoyl-$\beta$-alanine, prepared as above. Immediately, the vial was transferred into a freeze-dryer and was refrozen sufficiently at $-40°$ C. for 60 minutes to obtain a two layer frozen product. The temperature was then raised to 10° C. over a period of 3 hours, and primary drying was conducted at 10° C. for 24 hours. Subsequently, the temperature was raised to 50° C. over 3 hours, and secondary drying was conducted at 50° C. for 10 hours. The resulting freeze-dried preparation had a good appearance.

On the other hand, as a Control, separately 5 ml of a 10% w/v aqueous solution of N-benzoyl-$\beta$-alanine and 5 ml of a 10% w/v aqueous solution of (5R, 6S, 8R)-2-[(3S)-1-acetimidoylpyrrolidin-3-yl-thio]-6-(1-hydroxyethyl)-2-carbapenem-3-carboxylic acid were combined, and the total of 10 ml was charged into a 20 ml vial. After freezing the mixture in a freeze-dryer at $-40°$ C. for 60 minutes, the temperature was raised to 10° C. over a period of 3 hours and primary drying was conducted at 10° C. However, it took 64 hours before the drying was complete. Subsequently, after the temperature had been raised to 50° C. over a period of 3 hours, secondary drying was conducted at 50° C. for 10 hours, but it was not possible to obtain a freeze-dried preparation having a good appearance.

These preparations and a powdery divided product (prepared by simple mixing of the two components) were subjected to comparative evaluations. The results are shown in Table 1.

As is apparent from Table 1, the time required for freeze-drying, the appearance of the dried product and the stability over time (residual percentage of main drug) for the product produced in accordance with the double layer freezing process of the present invention were found to be much better than the values for those produced by the mixing method (Control). Also, the stability over time (main drug residual percentage) of the dried product produced in accordance with the process of the present invention was found to be much better than those of the powdery divided product (Control).

TABLE 1

| | Freeze-drying | | Stability (main drug residual percentage at 40° C. for 6 months) |
|---|---|---|---|
| | Required time | Appearance of dried product | |
| Double layer freeze-dried product | 40 Hr | Good | 97% |
| Mixing freeze-dried product (Control) | 80 Hr | Syrupy at bottom | 93% |
| Powdery divided product (Control) | — | — | 88% |

EXAMPLE 2

Preparation of a drug with poor stability when mixed 10 ml of a 30% w/v aqueous solution of S-adenosyl-L-methionine sulfate tosylate (the main drug, for which the conventional name, which is used hereinafter is "ademethionine", and which exhibits a eutectic point of $-35°$ C.) was charged into a 30 ml vial. It was then frozen in a freezing chamber at $-40°$ C. for 60 minutes to form a lower layer. Separately, 10 ml of a 0.18M aqueous solution of sodium monohydrogenphosphate was cooled to 5° C. and was then added onto the frozen layer of Ademethionine; it was then immediately frozen in a freezing chamber at −40° C. for 60 minutes to give a double layer frozen product. The vial was then transferred into a freeze-dryer, where primary drying was conducted at 10° C. for 48 hours and secondary drying at 40° C. for 10 hours. The resulting freeze-dried preparation had a good appearance.

On the other hand, as a Control, separately 10 ml of a 30% w/v aqueous solution of Ademethionine and 10 ml of a 0.18M aqueous solution of sodium monohydrogenphosphate were combined, and the total of 20 ml was charged into a 30 ml vial and frozen to −40° C. in a freeze-dryer, followed by freezing and drying under the same conditions. The results are shown in Table 2.

TABLE 2

|  |  | Double layer freeze-dried product | Mixing freeze-dried product (Control) |
|---|---|---|---|
| pH of adjusted solution | upper layer | 8.6 | 4.0 |
|  | lower layer | 0.7 |  |
| pH of dried product solution |  | 4.0 | 4.0 |
| time required for freeze-drying |  | 60 hours | 60 hours |
| dried product appearance |  | good | poor |
| Main drug residual percentage |  | 98% | 5% |

As is apparent from Table 2, a remarkable improvement was observed in the dried product appearance and the stability over time (main drug residual percentage) of the product produced by the double layer freezing method of the present invention as compared with those produced by the mixing freeze-drying method of the Control.

EXAMPLE 3

Preparation of a drug with poor stability as Na salt 2 ml of a 10% w/v aqueous solution of L-ascorbic acid were charged into a 10 ml vial and were then frozen in a freezing chamber at −40° C. for 60 minutes to form a lower layer. Separately, 2 ml of a 4.8% w/v aqueous solution of sodium hydrogencarbonate were cooled to 5° C., and the cooled solution was added to the frozen layer of ascorbic acid solution and frozen at −40° C. in a freeze-dryer to give a double layer frozen product. The vial was subjected to primary drying at 10° C. for 24 hours and secondary drying at 40° C. for 5 hours. The result was a freeze-dried preparation having a good appearance.

Meanwhile, as a Control, separately 2 ml of a 10% w/v aqueous solution of L-ascorbic acid and 2 ml of a 4.8% w/v aqueous solution of sodium hydrogencarbonate were combined, and the total of 4 ml was charged into a 10 ml vial, frozen to −40° C. in a freeze-dryer, and then freeze-dried under the same conditions as were used for the process of the invention.

These preparations and a powdery divided product consisting simply of sodium ascorbate were subjected to comparative evaluations. The results are shown in Table 3. In the Table, the products tested are identified as follows:

Product 1 is the double layer freeze-dried product of the present invention;
Product 2 is the product produced by freeze-drying a mixed solution (Control); and
Product 3 is the powdery divided product consisting of sodium ascorbate (Control).

TABLE 3

| Product |  | 1 | 2 | 3 |
|---|---|---|---|---|
| pH of adjusted solution | upper layer, | 9.8 | 7.5 | — |
|  | lower layer, | 3.6 |  |  |
| pH of dried product solution |  | 7.5 | 7.5 | 7.5 |
| time required for freeze-drying |  | 30 hours | 30 hours | — |
| dried product appearance |  | good | slightly discolored, yellow | poor |
| Main drug residual percentage |  | 98% | 90% | 88% |
| Appearance after 6 months at 40° C. |  | good | discolored, yellow | discolored, yellow |

As is apparent from Table 3, the appearance of the dried product and the stability over time (appearance and main drug residual percentage) of the product produced in accordance with the double layer freeze-drying method of the Example were both much better than those of the product produced by the mixing freeze-drying method of the Control. Also, the stability over time (appearance and main drug residual percentage) of the product produced in accordance with the double layer freeze-drying method of the Example was found to be much better than that of the powdery divided product of the Control. Sodium ascorbate itself is known to have poor stability.

EXAMPLE 4

Preparation of triple layers

This is an example of a multi-vitamin preparation, containing vitamins which are normally regarded as mutually incompatible, but which may be made compatible by forming a multi-layer product by the process of the invention.

The first of the layers was formed from "Solution 1", whose recipe is shown in Table 4. More specifically, a nonionic surfactant HCO-60 (trade name; manufactured by Nikko Chemicals Co. Ltd.) was added to the prescribed amounts of retinol palmitate, cholecalciferol, tocopherol acetate and menatetrenone to effect solubilization in distilled water, further mannitol was added and dissolved therein, and the total amount was made up to 50 ml with distilled water.

The next of the layers was formed from "Solution 2", whose recipe is shown in Table 5. More specifically; the prescribed amounts of thiamine hydrochloride, sodium riboflavin phosphate, pyridoxine hydrochloride, cyancovalamine, nicotinamide, panthenol and biotin were dissolved in distilled water, the resulting solution was adjusted to a pH value of 5.5 to 6.5 by the addition of sodium hydrogencarbonate and the total amount was made up to 50 ml with distilled water.

The third of the layers was formed from "Solution 3", whose recipe is shown in Table 6. More specifically, the prescribed amount of ascorbic acid was dissolved in distilled water and the total amount was made up to 20 ml.

TABLE 4

| Retinol palmitate | 50,000 IU |
|---|---|
| Cholecalciferol | 4,000 IU |
| Tocopherol acetate | 50 mg |

TABLE 4-continued

| | |
|---|---|
| Menatetrenone | 40 mg |
| Surfactant HCO-60 | 2,000 mg |
| Mannitol | 2,000 mg |
| Distilled water | Total 50 ml |

Of the ingredients listed in the above Table, the first 4 are lipophilic, and the surfactant is used to solubilize them in water.

TABLE 6

| | |
|---|---|
| Thiamine hydrochloride | 50 mg |
| Sodium riboflavin phosphate | 50 mg |
| Pyridoxine hydrochloride | 75 mg |
| Folic acid | 4 mg |
| Nicotinamide | 600 mg |
| Panthenol | 50 mg |
| Biotin | 2 mg |
| Distilled water | Total 50 ml |
| Ascorbic acid | 2,000 mg |
| Distilled water | 20 ml |

The ingredients in the above Table are all water-soluble.

The optimum pH of a solution of ascorbic acid is different from the optimum pH of the ingredients listed in Table 5.

5 ml Of Solution 1 were charged into a 25 ml vial and frozen in a freezing chamber at −40° C. for 60 minutes. Next, 5 ml of Solution 2 were charged onto the frozen layer of Solution 1 and again frozen in a freezing chamber at −40° C.. Finally, 2 ml of Solution 3 were charged onto the frozen layer of Solution 2 and then frozen in a freezing chamber at −40° C. to freeze the triple layers.

The vial was then transferred into a freeze-dryer, after which primary drying was conducted at a shelf temperature of 0° C. for 30 hours, and secondary drying at 30° C. for 10 hours. The result was a freeze-dried preparation having a good appearance.

Meanwhile, as a Control, a total of 12 ml (made up of 5 ml of Solution 1, 5 ml of Solution 2 and 2 ml of Solution 3) was charged into a vial, mixed, and then frozen in a freeze dryer to −40° C. Primary drying was conducted at −30° C. (drying at higher than −30° C. was impossible because the state of the product became syrupy) for 60 hours and secondary drying at 30° C. for 10 hours. The results are shown in Table 7.

TABLE 7

| | Triple layer freeze-dried product | | Mixing freeze-dried product (Control) |
|---|---|---|---|
| pH of adjusted solution | upper layer | 3.4 | 5.8 |
| | intermediate layer | 6.0 | |
| | lower layer | 6.0 | |
| pH of dried product solution | | 5.8 | 5.8 |
| time required for freeze-drying | | 45 hours | 75 hours |
| dried product appearance | | good | poor |
| Main drug residual percentage | Menatetrenone | 95% | 82% |
| | Biotin | 99% | 79% |
| | Ascorbic acid | 98% | 80% |
| Appearance after 6 months at 40° C. | | good | very poor |

As is apparent from Table 7, the time required for freeze-drying, the dried product appearance and the stability over time (appearance and main drug stability) of the product produced by the triple layer freeze-drying method of the Example were all much better than those of the products produced by the mixing freeze-drying method of the Control.

EXAMPLE 5

Preparation of a divided water layer

"Solution 1" was simply distilled water. "Solution 2" has the composition shown in Table 8:

TABLE 8

| | |
|---|---|
| Retinol palmitate | 50,000 IU |
| Cholecalciferol | 4,000 IU |
| Menatetrenone | 40 mg |
| Surfactant HCO-60 | 2,000 mg |
| Dextran 40 | 500 mg |
| Distilled water | Total 50 ml |

It was prepared by adding a nonionic surfactant, HCO-60 (trade name; manufactured by Nikko Chemicals Co. Ltd.), to the prescribed amounts of retinol palmitate, cholecalciferol and menatetrenone to effect solubilization in distilled water, dissolving dextran 40 in the solution and then making up the total amount to 50 ml by the addition of distilled water.

2 ml of distilled water were charged as Solution 1 into a 20 ml vial, and this was frozen in a freezing chamber at −40° C. to form a lower layer. Onto the frozen layer of Solution 1 were charged 5 ml of Solution 2, and this was frozen in a freezing chamber at −40° C. The vial was transferred into a freeze-dryer, and primary drying was conducted at a shelf temperature of 0° C. and secondary drying at a shelf temperature of 30° C.

Meanwhile, as a Control, 5 ml of the solution having the recipe shown in Table 8 were charged into a 20 ml vial, which was transferred into a freeze-dryer and frozen to −40° C., after which it was freeze-dried under the same conditions. The required times for each of the respective steps were measured.

The results are shown in Table 9.

As is apparent from Table 9, the required time for freeze-drying according to the double layer freeze-drying method of the Example is clearly much shorter than that required for the mixing freeze-drying method of the Control.

TABLE 9

| | Freeze-drying time | |
|---|---|---|
| | Primary freeze-drying time (0° C.) | Secondary freeze-drying time (30° C.) |
| Double layer freeze-dried product | 24 Hr | 10 Hr |
| Mixing freeze-dried product (Control) | 48 Hr | 10 Hr |

EXAMPLE 6

Preparation of one container in place of two containers 2.5 ml of an aqueous solution containing 400 μg/ml of carboquone (an anti-cancer drug) were charged into a 10 ml vial and frozen in a freezing chamber at −40° C. for 60 minutes to form a lower layer. Separately, 1 ml of a 0.1M aqueous solution of sodium monohydrogenphosphate (pH 7.2) was cooled was charged onto the above frozen layer and frozen in a freeze-dryer at −40° C. for 60 minutes. This was subjected to primary drying at 0° C. for 24 hours, and then to secondary drying at 30° C. for 10 hours. The resulting freeze-dried preparation had a good appearance.

Meanwhile, as a Control, a total of 3.5 ml [made up of 2.5 ml of a 400 μg/ml aqueous solution of carboquone and 1 ml of a 0.1M aqueous solution of sodium monohydrogenphosphate (pH 7.2)] were charged into a 10 ml vial, and freeze-dried under the same conditions as described above for the process of the invention.

The carboquone contents were measured for each of the preparations obtained. The results are shown in Table 10.

As is apparent from Table 10, the stability (main drug residual percentage) of the product produced by the double layer freeze-drying method of the Example was found to be much better than that of the product produced by the mixing freeze-drying method of the Control.

TABLE 10

|  | Carboquone content* (%) | pH after dissolution |
|---|---|---|
| Double layer freeze-dried product | 100 | 7.2 |
| Mixing freeze-dried product (Control) | 85 | 7.2 |

*Residual percentage based on the amount of 2 mg/vial

In the prior art, it has been found that aqueous solutions of carboquone are most stable at pH values of from 7.0 to 7.4. However, when carboquone is freeze-dried in a phosphate buffer at a pH value of 7.2, carboquone decomposes due to the change in pH (from 7.2 to 4.2) during freezing [D.L. Williams; Biochem. J., 167, 593-600 (1977)]. Thus, freezing in the same container was impossible. Accordingly, in the prior art, carboquone is supplied alone as a freeze-dried preparation in association with a phosphate buffer of pH 7.2.

Thus, the following advantages can be seen to be achieved by the process of the present invention:

(1) A drug which is difficult to freeze-dry can be obtained as a freeze-dried preparation within a relatively short time.

(2) A drug which is difficult to freeze-dry can be obtained as a freeze-dried preparation with a good appearance.

(3) Stability over time is improved as compared with the conventional mixing of two or more freeze-dried preparations.

(4) A drug which is unstable due to the mutual interaction of two or more of its components can be obtained as a stable combined preparation.

(5) The combined preparation of the prior art in which a freeze-dried material is associated with a dissolved solution can be replaced by a one container freeze-dried preparation.

We claim:

1. A method of preparing a freeze-dried preparation in which a first liquid is frozen, a second liquid is added to the frozen first liquid and is frozen thereon, and the frozen first and second liquids are freeze-dried together, in which at least one of said first and second liquids contains a pharmaceutical compound or preparation dissolved or suspended therein.

2. The method of claim 1, wherein each of said liquids is an aqueous liquid.

3. The method of claim 2, wherein one of said first and said second liquids is water and the other is an aqueous solution of said pharmaceutical compound or preparation.

4. The method of claim 2, wherein each of said first and said second liquids is an aqueous solution of a physiologically active substance.

5. The method of claim 1, wherein a third liquid is added to the frozen first and second liquids and is frozen thereon, and the frozen first, second and third liquids are freeze-dried together.

6. The method of claim 5, wherein each of said liquids is an aqueous liquid.

7. The method of claim 6, wherein one of said first, second and third liquids is water and the others are aqueous solutions of pharmaceutical compounds or preparations.

8. The method of claim 6, wherein each of said first, second and third liquids is an aqueous solution of a physiologically active substance.

9. The method of claim 1, wherein said first liquid is frozen to a temperature of from $-10°$ C. to $-50°$ C.

10. The method of claim 1, wherein said temperature is from $-30°$ C. to $-50°$ C.

11. The method of claim 1, wherein said temperature is about $-40°$ C.

12. The method of claim 1, wherein the total thickness of all frozen layers does not exceed 40 mm.

13. The method of claim 1, wherein each layer is of thickness at least 1 mm.

14. The method of claim 13, wherein each layer is of thickness at least 2 mm.

15. The method of claim 1, wherein said pharmaceutical compound is a drug.

16. The method of claim 1, wherein said pharmaceutical compound is a vitamin.

17. The method according to claim 1, wherein the pharmaceutical compound is selected from the group consisting of antibiotics, analgesics, anti-inflammatory agents, anti-cancer drugs and vitamins.

18. The method of claim 1, wherein one of said liquids comprise N-benzoyl-beta alanine.

19. The method of claim 1, wherein one of said liquids comprise (5R, 6S, 8R)-2-((3S)-1-acetimidoylpyrrolidin-3-yl-thio) -6-(1-hydroxyethyl)-2-carbapenem-3-carboxylic acid.

20. The method of claim 1, wherein the first liquid is an aqueous solution of N-benzoyl-beta-alanine and the second liquid is an aqueous solution of (5R, 6S, 8R)-2-((3S)-1-acetimidoylpyrrolidin-3-yl-thio) -6-(1-hydroxyethyl)-2-carbapenem-3-carboxylic acid.

21. The method of claim 20, wherein said aqueous solution of N-benzoyl-beta-alamine is frozen at $-40°$ C., said aqueous solution of (5R, 6S, 8R)-2-((3S)-1-acetimidoylpyrrolidin-3-yl-thio) -6-(1-hydroxyethyl)-2-carbapenem-3-carboxylic acid is cooled to $5°$ C. and said cooled solution is added to the resultant frozen layer of N-benzoyl-beta-alanine and refrozen at $-40°$ C.

22. The method of claim 1, wherein one of said liquids comprises S-adenosyl-L-methionine sulfate tosylate.

23. The method of claim 1, wherein the first liquid is an aqueous solution of S-adenosyl-L-methionine sulfate tosylate and the second liquid is an aqueous solution of sodium monohydrogenphosphate.

24. The method of claim 1, wherein one of said liquids comprise L-ascorbic acid.

25. The method of claim 1, wherein the first liquid is an aqueous solution of L-ascorbic acid and the second liquid is an aqueous solution of sodium hydrogencarbonate.

26. The method of claim 5, wherein the first liquid comprises retinol palmitate, cholecalciferol, tocopherol acetate, menatetrenone, a nonionic surfactant, mannitol and distilled water, the second liquid comprises thiamine hydrochloride, sodium riboflavin phosphate, pyridoxine hydrochloride, folic acid, nicotinamide, panthenol, biotin and distilled water and the third liquid comprises ascorbic acid and distilled water.

27. The method of claim 1, wherein one of said liquids comprise a solution comprising retinol palmitate, cholecalciferol, tocopherol acetate, menatetrenone and mannitol.

28. The method of claim 1, wherein one of said liquids comprise a solution comprising thiamine hydrochloride, sodium riboflavin phosphate, pyridoxine hydrochloride, folic acid, nicotinamide, panthenol and biotin.

29. The method of claim 1, wherein the first liquid comprises distilled water and the second liquid comprises retinol palmitate, cholecalciferol, menateterone, a non-ionic surfactant, distilled water and dextran.

30. The method of claim 1, wherein the first liquid is an aqueous solution of carboquone and the second liquid is an aqueous solution of sodium monohydrogenphosphate.

31. The method of claim 1, wherein one of said liquids comprise carboquone.

32. The method of claim 5, wherein one of said liquids comprise carboquone.

33. A method of preparing a freeze-dried preparation in which a first aqueous liquid is frozen to a temperature of from $-10°$ C. to $-50°$ C., a second aqueous liquid is added to the frozen first liquid without melting the frozen first liquid and is frozen thereon, and the frozen first and second liquids are freeze-dried together, in which at least one of said first and second liquids contains a pharmaceutical compound or preparation dissolved or suspended therein.

34. A method of preparing a freeze-dried preparation in which a first aqueous liquid is frozen to a temperature of from $-10°$ C. to $-50°$ C., a second aqueous liquid is added to the frozen first liquid without melting the frozen first liquid and is frozen thereon to a temperature of from $-10°$ C. to $-50°$ C., a third aqueous liquid is added to the frozen first and second liquids without melting the frozen first and second liquids and is frozen thereon, and the frozen first, second and third liquids are freeze-dried together, in which at least one of said first, second and third liquids contains a pharmaceutical compound or preparation dissolved or suspended therein.

* * * * *

UNITED STATES PATENT AND TRADEMARK OFFICE
CERTIFICATE OF CORRECTION

PATENT NO. : 5,044,091

DATED : September 3, 1991

INVENTOR(S) : UEDA et al

It is certified that error appears in the above-identified patent and that said Letters Patent is hereby corrected as shown below:

Column 1, line 11, after "example", insert -- , --.

Column 4, line 47, after "such as", insert -- a --.

Column 9, line 11, change "TABLE 6" to read --TABLE 5--; and delete the following last two lines:

```
" Ascorbic acid          2,000 mg
  Distilled water          20 ml "
```

Column 9, line 21, after "TABLE 5", insert the following :

```
    --              TABLE 6
         _____

Ascorbic acid         2,000 mg
         Distilled water         20 ml      --.
```

Signed and Sealed this

Seventeenth Day of August, 1993

Attest:

BRUCE LEHMAN

Attesting Officer

Commissioner of Patents and Trademarks

UNITED STATES PATENT AND TRADEMARK OFFICE
CERTIFICATE OF CORRECTION

Reexamination
Certificate No.: B1 5,044,091
DATED : December 30, 1997
INVENTOR(S) : Seigo UEDA et al.

It is certified that error appears in the above-indentified Reexamination Certificate and that said Reexamination Certificate is hereby corrected as shown below:

On the title page
Item [56], under the heading "References Cited U.S. PATENT DOCUMENTS", replace "Chang et al." with --Cheng et al.--.

In the right-hand column of the Title Page, first line thereof, replace "4,802,287" with --4,802,286--.

In the right-hand column of the Title Page, Item [56}, under the heading "OTHER PUBLICATIONS",
    line 4, replace "the Lyophilization" with --The Lyophilization--;
    line 7, replace "effect" with --Effect--;
    line 8, replace "drying" with --Drying--; and
    line 9, replace "science" with --Science--.

Signed and Sealed this

Twenty-eighth Day of April, 1998

Attest:

BRUCE LEHMAN

*Attesting Officer*

*Commissioner of Patents and Trademarks*

REEXAMINATION CERTIFICATE (3405th)

United States Patent [19]
Ueda et al.

[11] B1 5,044,091
[45] Certificate Issued Dec. 30, 1997

[54] METHOD OF PREPARING A FREEZE-DRIED FORMULATION OF A DRUG

[75] Inventors: Seigo Ueda; Kunio Hashi; Takashi Shiokari; Akira Kusai, all of Shinagawa, Japan

[73] Assignee: Sankyo Company, Limited, Tokyo, Japan

Reexamination Request:
No. 90/003,743, Feb. 27, 1995

Reexamination Certificate for:
Patent No.: 5,044,091
Issued: Sep. 3, 1991
Appl. No.: 509,967
Filed: Apr. 16, 1990

Certificate of Correction issued Aug. 17, 1993.

[30] Foreign Application Priority Data

Apr. 18, 1989 [JP] Japan ........................ 1-98561

[51] Int. Cl.$^6$ ........................................ F26B 5/06
[52] U.S. Cl. .................................... 34/303; 34/92
[58] Field of Search ...................... 34/92, 284, 285, 34/287, 289, 295, 303, 406

[56] References Cited

U.S. PATENT DOCUMENTS

| | | | |
|---|---|---|---|
| 3,269,905 | 8/1966 | Damaskus et al. | 206/459.5 |
| 4,178,695 | 12/1979 | Erbeia | 34/295 |
| 4,430,807 | 2/1984 | Davis et al. | 34/342 |
| 4,433,558 | 2/1984 | Chang et al. | 62/537 |
| 4,470,202 | 9/1984 | Buxton et al. | 34/284 |
| 4,754,597 | 7/1988 | Buxton et al. | 345/287 |
| 4,802,287 | 2/1989 | Kobayashi et al. | 34/92 |
| 5,044,091 | 9/1991 | Ueda et al. | 34/92 |

FOREIGN PATENT DOCUMENTS

| | | |
|---|---|---|
| 211257 | 2/1987 | European Pat. Off. |
| 2109201 | 5/1972 | France |
| 61-68412 | 4/1986 | Japan |
| 62-29513 | 2/1987 | Japan |
| 63-28892 | 6/1988 | Japan |
| 797774 | 7/1958 | United Kingdom |

OTHER PUBLICATIONS

*Bulletin of the Parenteral Drug Association*, Benito Couriel, "Advances in Lyophilization Technology", Sep.–Oct. 1977, vol. 31, No. 5, pp. 227–236.

Williams et al., "the Lyophilization of Pharmaceuticals: A Literature Review", J. Parenteral Science and Technology, 38, pp. 48–59, Mar. 1984.

Koyama et al, "effect of Solvent Addition and Thermal Treatment of Freeze drying of Cefazolin Sodium", Japan Parenteral science and Technology, 42, pp. 47–52, Mar. 1988.

Journal of The Japanese Society For Research of Freezing and Drying, 22, pp. 48–55, Jan. 1976.

Farumashi, 5, vol. 5, No. 2, pp. 99–102, Feb. 1969.

*Primary Examiner*—Willis R. Wolff, Jr.

[57] ABSTRACT

In a freeze-drying method for producing a dried pharmaceutical compound or preparation, a first liquid is frozen, a second liquid is added to the frozen first liquid and is frozen thereon, and the frozen first and second liquids are freeze-dried together, in which at least one of said first and second liquids contains said pharmaceutical compound of preparation dissolved or suspended therein. The other liquid or liquids may be pure solvent (generally water) or may contain one or more other substances.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 3–8 and 15–34 are cancelled.

Claims 2, and 9–14 are determined to be patentable as amended.

New claims 35–41 are added and determined to be patentable.

2. The method of claim [1] *35*, wherein each of said *first and second* liquids is an aqueous liquid.

9. The method of claim [1] *35*, wherein said first liquid is frozen to a temperature of from –10° C. to –50° C.

10. The method of claim [1] *9*, wherein said temperature is from –30° C. to –50° C.

11. The method of claim [1] *9*, wherein said temperature is about –40° C.

12. The method of claim [1] *35*, wherein the total thickness of all frozen layers does not exceed 40 mm.

13. The method of claim [1] *35*, wherein each layer is of thickness at least 1 mm.

14. The method of claim 13, wherein each layer is of a thickness *of* at least 2 mm.

*35. A method of preparing a freeze-dried preparation-in which at least one of a first liquid and a second liquid contains a pharmaceutical compound or preparation dissolved or suspended therein, wherein the first liquid contains N-benzoyl-β-alanine and is frozen to form a frozen first liquid at a temperature low enough to withstand heat from the second liquid which contains (5R, 6S, 8R)-2-[(3S)-1-acetimidoylpyrrolidin-3-yl-thio]-6-(1-hydroxyethyl)-2-carbapenem-3-carboxylic acid, and the second liquid is cooled, then added onto the frozen first liquid, thereon frozen at a temperature low enough to form a frozen second liquid, and the frozen first liquid and the frozen second liquid are freeze-dried together to prepare a two layer freeze-dried product.*

*36. The method of claim 35, wherein said second liquid is cooled at 5° C. and then added to the frozen first liquid.*

*37. The method of claim 11, wherein said second liquid is cooled at 5° C. and then added on the frozen first liquid.*

*38. The method of claim 2, wherein said first liquid is frozen at –40° C. for 60 minutes and said second liquid is cooled to 5° C. and added to said frozen first liquid and refrozen at –40° C. for 60 minutes.*

*39. The method of claim 35, which further comprises raising the temperature of the two layer freeze-dried product to 10° C., over a period of time of 3 hours and then carrying out drying at a temperature of 50° C. for 10 hours.*

*40. The method of claim 2, which further comprises raising the temperature of the two layer freeze-dried product to 10° C., over a period of time of 3 hours and then carrying out drying at a temperature of 50° C. for 10 hours.*

*41. The method of claim 38, which further comprises raising the temperature of the two layer freeze-dried product to 10° C., over a period of time for 3 hours and then carrying out drying at a temperature of 50° C. for 10 hours.*

* * * * *